United States Patent [19]
Eaton

[11] Patent Number: 5,951,602
[45] Date of Patent: Sep. 14, 1999

[54] INTERNAL FIXATION RETENTION FOR OSSEOINTEGRATION

[75] Inventor: L. Daniel Eaton, Little Rock, Ark.

[73] Assignee: Board of Trustees of the University of Arkansas

[21] Appl. No.: 09/123,156

[22] Filed: Jul. 27, 1998

[51] Int. Cl.⁶ ............................... A61F 2/02; A61F 2/18; A61F 2/14; A61F 2/10; A61F 2/28
[52] U.S. Cl. ............................... 623/11; 623/11; 623/10; 623/4; 623/15; 623/16
[58] Field of Search .................... 623/11, 10, 4, 623/15, 16

[56] References Cited

U.S. PATENT DOCUMENTS

| D. 294,295 | 2/1988 | Branemark | D24/33 |
|---|---|---|---|
| 4,713,003 | 12/1987 | Symington et al. | 433/173 |
| 4,976,739 | 12/1990 | Duthie, Jr. | 623/16 |
| 5,064,374 | 11/1991 | Lundgren | 433/173 |
| 5,344,457 | 9/1994 | Pilliar et al. | 623/16 |
| 5,376,323 | 12/1994 | Eaton | 264/222 |
| 5,425,763 | 6/1995 | Stemmann | 623/11 |
| 5,593,444 | 1/1997 | Svensson et al. | 623/16 |

OTHER PUBLICATIONS

Tjellström, et al., "Maxillofacial Reconstruction and Hearing Rehabilitation—Surgeons Manual," University of Göteborg, Göteborg, Sweden, date unknown.
Product Catalogue, Branemark System, Nobelpharma AB, 1995.
Holgers, et al., Morphological Evaluation of Clinical Long–Term Percutaneous Titanium Implants, The International Journal of Oral and Maxillofacial Implants, vol. 9, No. 6, 1994, pp. 689–697.
Granstrom, et al., "A Detailed Analysis of Titanium Implants Lost in Irradiation Tissues," The International Journal of Oral and Maxillofacial Implants, vol. 9, No. 6, 1994, pp. 653–662.
Eriksson, et al, "Osseointegration from the Perspective of the Plastic Surgeon," Plastic and Reconstructive Surgery, Mar. 1994, pp. 626–637.
Holt, "Osseointegrated Implants in Oro–Dental and Facial Prosthetic Rehabilitation," Craniofacial Skeletal Augmentation and Replacement, Otolarynogologic Clinics of North America, vol. 27, No. 5, Oct. 1994, pp. 1001–1014.
Tjellstrom, "Osseointegrated Implants for Replacement of Absent or Defective Ears," Clinics in Plastic Surgery, vol. 17, No. 2, Apr. 1990, pp. 355–366.
Product Catalog, Cranio–facial Rehabilitation, Nobelpharma AB, 1991.
"Guidelines for Simulated Surgical Training," Nobelphorma AB, Göteborg, Sweden, date unknown.

*Primary Examiner*—Mickey Yu
*Assistant Examiner*—Alvin Stewart
*Attorney, Agent, or Firm*—Ray F. Cox, Jr.

[57] ABSTRACT

A combination prosthesis and osseointegrated fixture for the attachment of the prosthesis. A percutaneous osseointegrated fixture is provided with a bar of biocompatible material. The bar is formed into a plurality of loops and the prosthesis is molded to form a plurality of complementary mushroom-headed protuberances that fit snapwise into the loops.

2 Claims, 8 Drawing Sheets

INTERNAL FIXATION RETENTION FOR OSSEOINTEGRATION

BACKGROUND OF THE INVENTION

The present invention relates to prosthetic devices, and in particular, to a combination prosthesis and osseointegrated internal fixation means.

Prostheses, such as artificial eyes, ears, and the like, require some means of attachment to the patient. Such attachments should be both functional and aesthetic. Aesthetic considerations require that the prosthesis look as nearly as possible identical to the patients natural anatomy. Functional considerations include a comfortable and secure fit and restoration of normal uses associated with the lost or damaged anatomy. Desirably, the fit of the prosthesis is secure but the prosthesis is removable as required by the patient.

One technique for attaching prostheses involves osseointegrated implants. Osseointegrated implants are surgically implanted into the patient's bony structure. These osseointegrated implants provide the anchoring point for the prosthesis.

Osseointegrated implants for the attachment of prostheses are known in various applications, including the fixation of dental prostheses and orbital prostheses. Typically, these osseointegrated implants include certain common elements. Usually, a screw shaped fixture, typically of titanium, is surgically implanted and allowed to osseointegrate into the bone. A skin penetrating element, an abutment, also typically of titanium, is attached to the screw shaped fixture. A well known osseointegrated implant of this type (known as the Branemark system) developed by Per-Ingvar Branemark is available through Nobelpharma AB, P0 Box 5190 S-402, Goteborg, Sweden.

U.S. Design Pat. No. Des.294,295 issued to Branemark illustrates a typical implant of the type employed in the Branemark system. In the Branemark system a gold bar is fastened laterally between two osseointegrated implants and externally to the patient's skin. Metallic clips embedded in the prosthesis are employed to removable attach the prosthesis by clipping onto the gold bar.

Another type of implant as used in conjunction with a spacing member for attaching a cranial facial prosthesis is disclosed in U.S. Pat. No. 5,593,444 issued to Svensson et al. Svensson et al. discloses a spacing member arranged between a securing element implanted in the facial bone and an extraoral prosthesis.

U.S. Pat. No. 5,064,374 issued to Lundgren discloses an implant structure comprising a central portion which can be attached to an implant fixed anchorage element and two projecting wing like structures to form a unitary bridge body.

In another type of fixation method, a pair of strong magnets may be employed, one affixed to the prosthesis and the other affixed to the osseointegrated implant. U.S. Pat. No. 5,425,763 discloses such a magnet arrangement for attaching prostheses to an osseointegrated implant.

There are a number of limitations to the prior art techniques for attaching a prosthesis to an osseointegrated implant. One is that the repeated attachment and removal of the prostheses can weaken the osseointegrated fixture. Another problem is that in some applications, such as orbital prostheses, limited space is available for fitting the prosthesis and fit is critical both for aesthetics and comfort. The prior art fixation techniques reduce the space available for the prosthesis.

These and other limitations of the prior art are overcome by the present invention.

SUMMARY OF THE INVENTION

In the prior art gold wire bars are attached to percutaneous fixtures attached to bone anchored to titanium implants. Prostheses, mid-face, temporal, or thoracic, are attached to the gold wire bars with clips or magnets. In order to secure the prostheses to the gold wire bars, however, the clips or magnets exert considerable holding force, which renders attachment or removal of the prostheses liable to weaken the bone implants. Furthermore, the prior art techniques require the attachment of the prostheses to the external side of the gold wire bars. This leads to the loss of volume within which the prosthesis may fitted and may also render naturalistic fitting of the prosthesis difficult or impossible.

The present invention is a combination prosthesis and fixture for the attachment of the prosthesis. The fixture comprises two or more osseointegrated implants and an attached bar. Each osseointegrated implant comprises an osseointegrated flange fixture to which an abutment, external to the patient's skin, is affixed. The bar is affixed to the abutments. The bar is formed into a plurality of loops. The prosthesis is formed of flexible synthetic material with "mushroom" headed protuberances that fit snapwise into the loops. With this approach, the prosthesis can be removed and reattached repeatedly without weakening the osseointegrated fixtures. The prosthesis may be formed by the method of U.S. Pat. No. 5,376,323. The prosthesis may be formed for a smooth close fit with the patient's anatomy. The formation of the "mushroom" does not significantly alter the surface contour of the portion of the prosthesis that contacts the patient.

Conforming the prosthesis closely to the patient's anatomy has the advantage of preserving humidity which may be significant is certain applications, such as the replacement of an excised eye. Furthermore, the prior art attachment methods generally place the prosthesis completely exterior to the fixture thus losing space that may be desirable for accommodating the prosthesis itself. For example, correct aesthetic placement of a prosthetic eye is critically dependent on placing the prosthetic eye in the same plane as the natural eye. The space lost by other methods between the fixture and the surface of the patient's anatomy is regained with the present invention and may be usefully employed in the placement of the prosthesis.

It is therefore an object of the present invention to provide for a prosthesis and osseointegrated fixture for the attachment of the prosthesis that is secure and repeatedly removable without weakening the osseointegrated implant.

It is a further object of the present invention to provide for a prosthesis and osseointegrated fixture for the attachment of the prosthesis which preserves volume adjacent to the patient's anatomy for the placement of the prosthesis.

These and other objects and advantages of the present invention will be apparent from a consideration of the following detailed description of the preferred embodiments in conjunction with the appended drawings as described following.

DETAILED DESCRIPTION OF THE PREFERRED EMBODIMENTS

Figure 1:
FIG. 1 is a view of the site of a patient's excised eye.

The present invention is a combination of a prosthesis and an osseointegrated fixture for the attachment of the prosthesis. Osseointegrated fixtures are integrated into the bone structure of the patient. Osseointegrated fixtures may be described with reference to FIGS. 1 and 2. FIG. 1 shows the site 10 of an excised eye, which may have been lost due to, e.g., trauma, congenital defect, or surgical removal of a neoplasm. Although the preferred embodiment described herein is described with reference to a prosthetic eye and related fixture, the present invention is not so limited. Other types of prostheses would be suitable for the practice of the present invention, including, but not limited to, ears and other portions of the craniofacial anatomy.

An osseointegrated implant typically comprises at least two parts, a flange fixture integrated into the bone and an abutment affixed to the flange fixture and external to the patient's skin. A typical flange fixture is disclosed in U.S. design Pat. No. Des.294,295, the disclosure of which is incorporated herein by reference. As used herein, the term "osseointegrated implant" refers to the combination of the flange fixture and the abutment.

Figure 2:
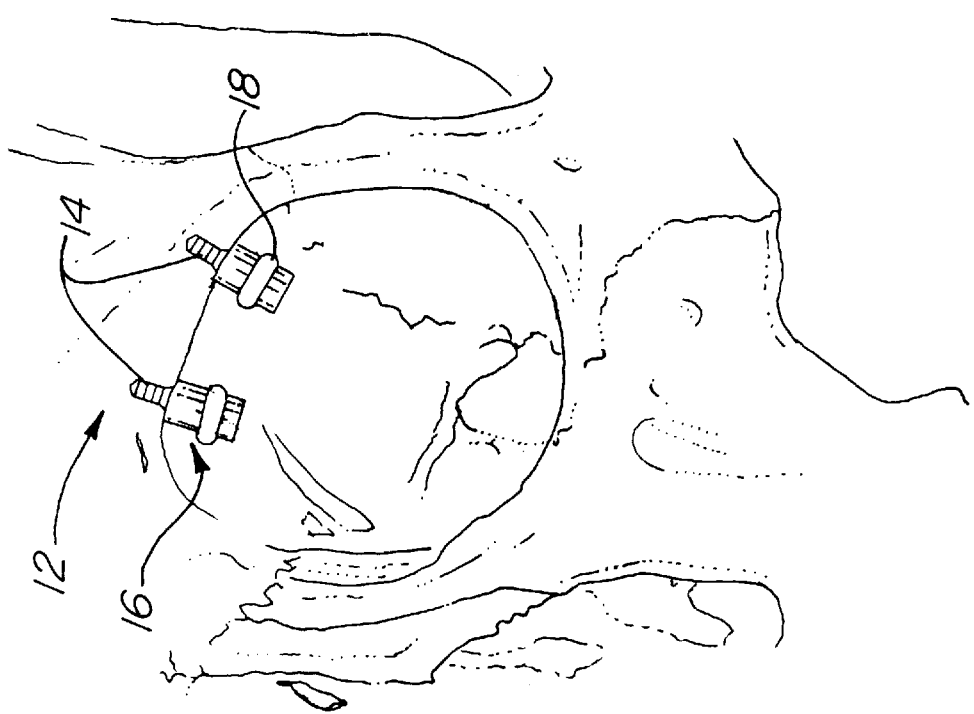
FIG. 2 is a view of the patient's orbit and surrounding bone structure showing the placement of osseointegrated implants.

The implantation begins with a determination of the appropriate location for the implant. In the example of FIGS. 1 and 2, the locations are in the orbital rim 12. The location should be chosen to avoid any problems with the placement of the prosthesis and with due consideration for aesthetic factors in the contour of the prosthesis. After removal of a flap of the patient's skin over the chosen location for an implant, a hole is drilled and tapped in the orbital rim 12. A flange fixture 14 is screwed into the drilled and tapped hole in the orbital rim 12. After the flange fixture 14 is inserted in the bone, it is allowed to integrate with the bone, i.e., the bone of the orbital rim 12 heals around the flange fixture 14. To assist in this process, the patient's skin is placed back over the top of the flange fixture 14 for a period of time. After healing and complete integration, the skin is removed and the second part of the osseointegrated implant 16, the abutment 18, is affixed to the flange fixture 14 by means of a screw (not shown).

Figure 4:
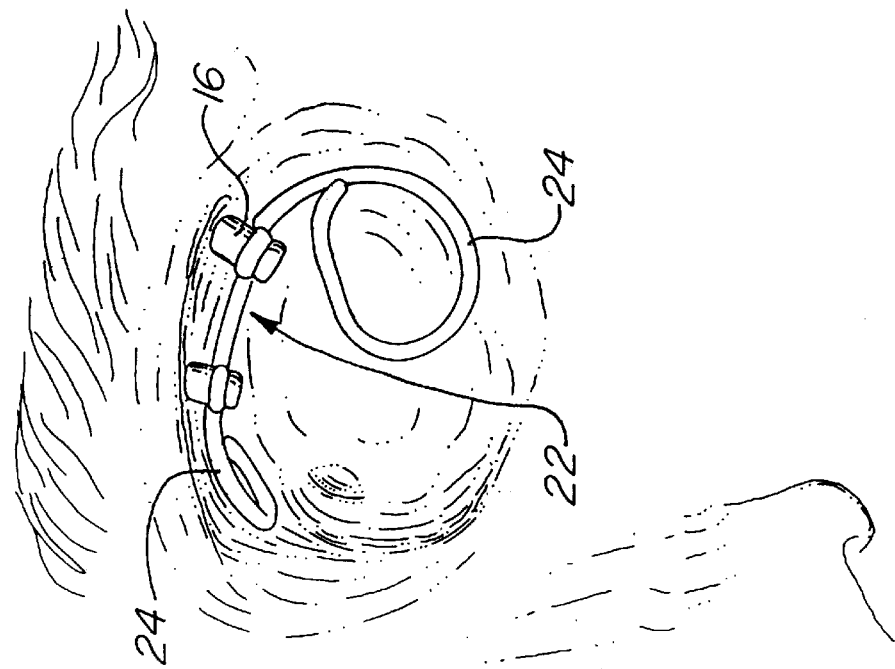
FIG. 4 is a view of the site of FIG. 1 showing the external appearance of the osseointegrated implants and bar.
Figure 3:
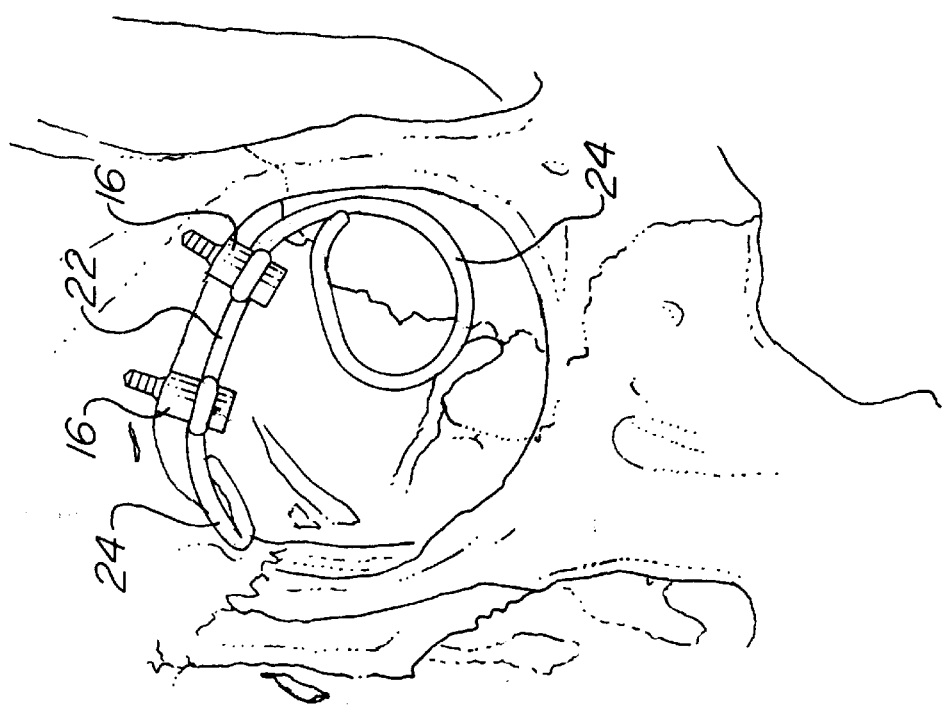
FIG. 3 is the view of FIG. 2 with the addition of a bar to the osseointegrated implants.
Figure 5:
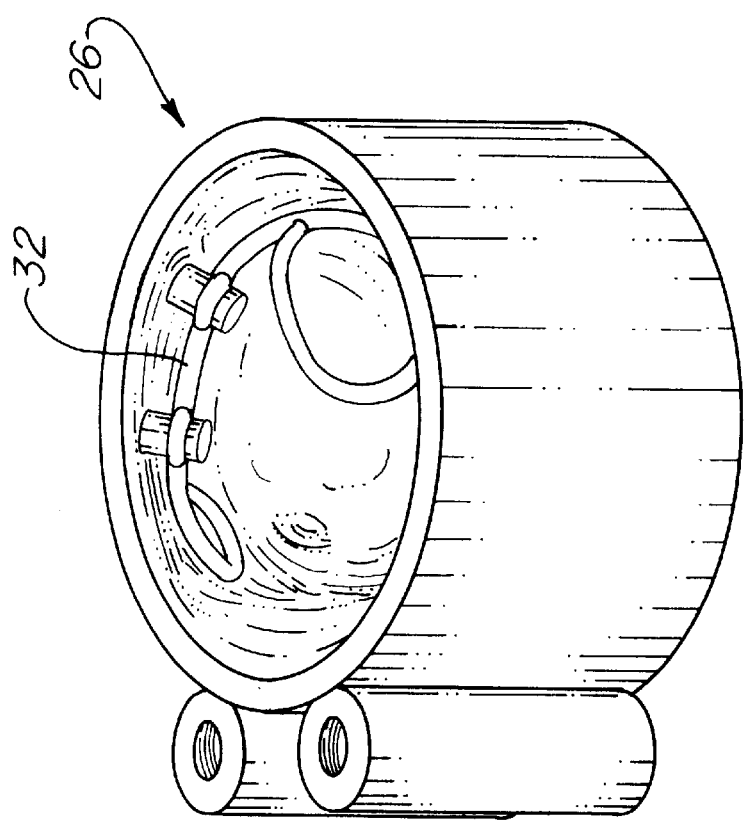
FIG. 5 is a perspective view of a lower part of a mold formed from an impression taken of the site of FIG. 4.

After a period of healing following placement of the abutment 18, the final steps in the preparation of the osseointegrated fixture 20 can commence as described with reference to FIGS. 3–5. Guide pins (not shown) are attached to the abutments 18 to locate the orientation of the axis of the implants 16. An impression is taken of the site 10 including the implants 16 and the guide pins. After the impression is set, the guide pins are unscrewed and the impression is removed. A cast 26 is then made from the impression.

A bar 22, preferably of gold alloy or other biocompatible material, is formed with at least two loops 24. The bar 22 may be fitted and shaped on the cast 26 prior to fitting it to the patient. Next the abutments 18 are removed from the flange fixtures 14 and welded to the bar 22 using the cast 26 as guide. Final fitting of the bar 22 may then be performed on the patient by attaching the welded bar 22 and abutments 18 to the flange fixtures 14 as shown in FIGS. 3 and 4.

With the looped bar 22 and welded abutments 18 attached to the flange fixtures 14, the thin space immediately behind the bar 22 is filled with wax. The wax is undercut slightly so that when an impression is taken as described hereinafter, the impression of the looped bar 22 partially, but not completely wraps around the looped bar 22.

Figure 6:
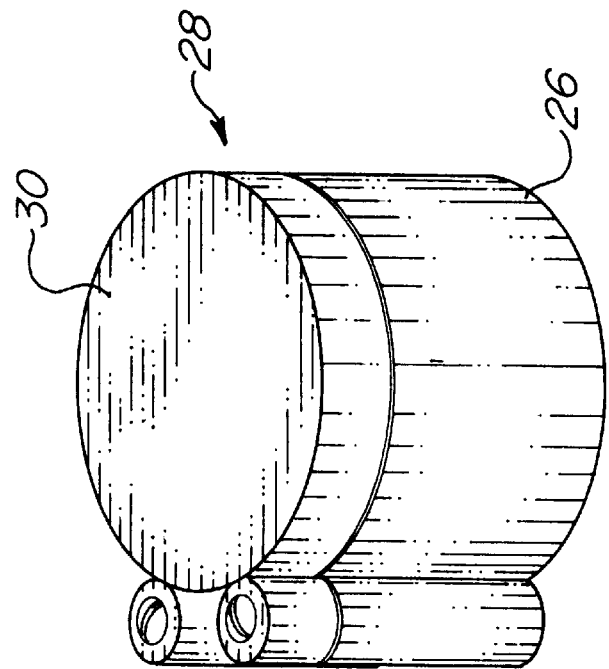
FIG. 6 is a perspective view of a mold with both the lower mold portion of FIG. 5 and an upper mold portion for forming the exterior anatomy of the prosthesis.
Figure 7:
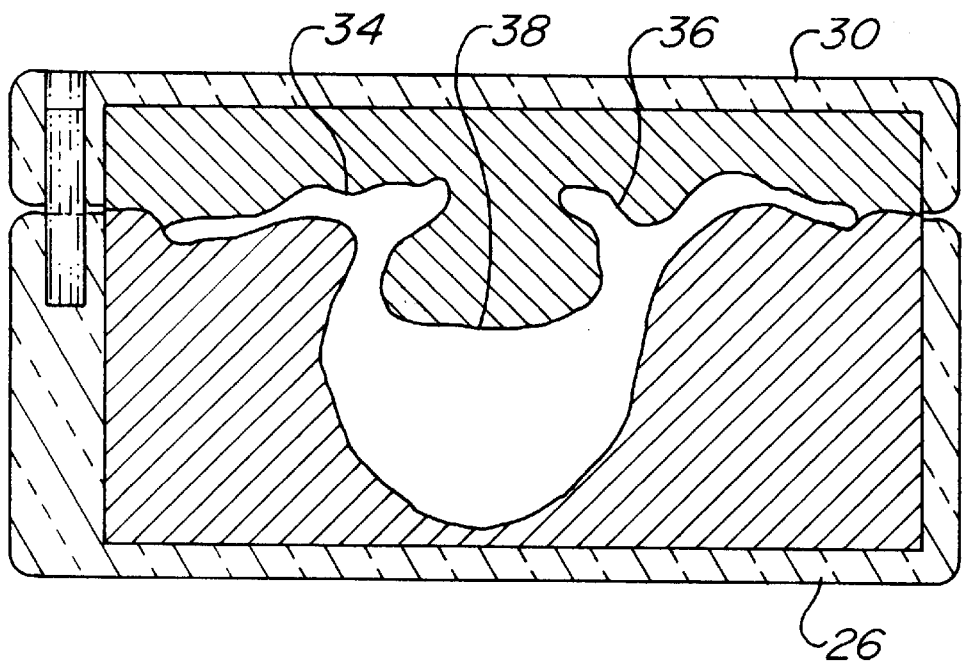
FIG. 7 is an elevational cross sectional view of the mold of FIG. 6.

The impression, using, for example, alginate, is then taken of the site 10 on the patient where the prosthesis is to be fitted. As shown in FIGS. 5–7, a cast in harder material, such as dental stone or plaster of paris, is taken from the impression and becomes the lower part 26 of a two-part mold 28 that is used to form the prosthesis. The lower part 26 may be seen to be an exact replica of the site 10 with a replica of the complete osseointegrated fixture 32 as it would appear on the patient. The osseointegrated fixture 32 comprises the flange fixtures 14 (although not appearing above the patient's skin), the abutments 18, and the looped bar 22.

Figure 8:
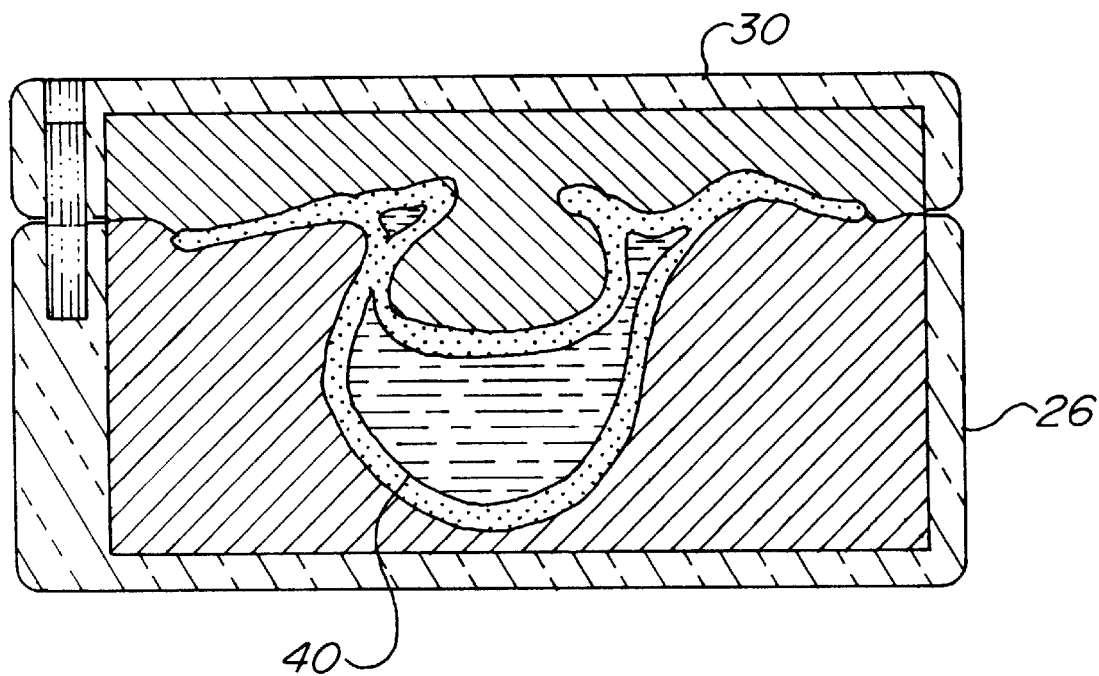
FIG. 8 is an elevational cross sectional view of the mold of FIG. 6 showing the injection of material to form the prosthesis.

The mold 28 also comprises an upper part 30 which forms the anterior portion of the prosthesis, including the superior and inferior eyelids 34, 36 and the recess 38 for receiving a prosthetic eye. From the two-part mold 28 the prosthesis 40 is prepared as shown in FIG. 8. The prosthesis 40 may be prepared using the room temperature vulcanizable (RTV) silicone method described in previous U.S. Pat. No. 5,376,323, the disclosure of which is incorporated herein by reference.

Figure 9:
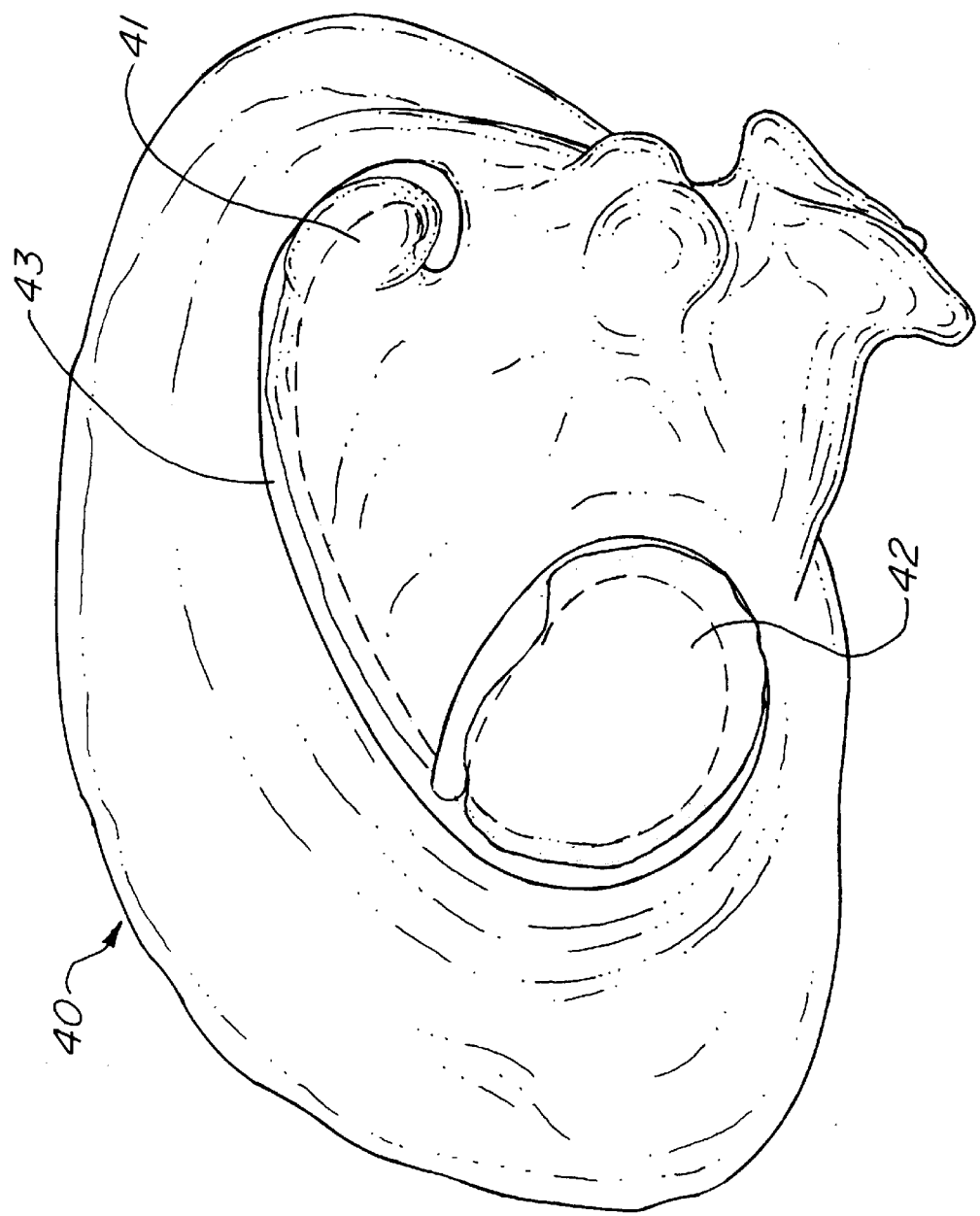
FIG. 9 is an elevation view of the anterior of the prosthesis formed from the mold of FIG. 6.
Figure 10:
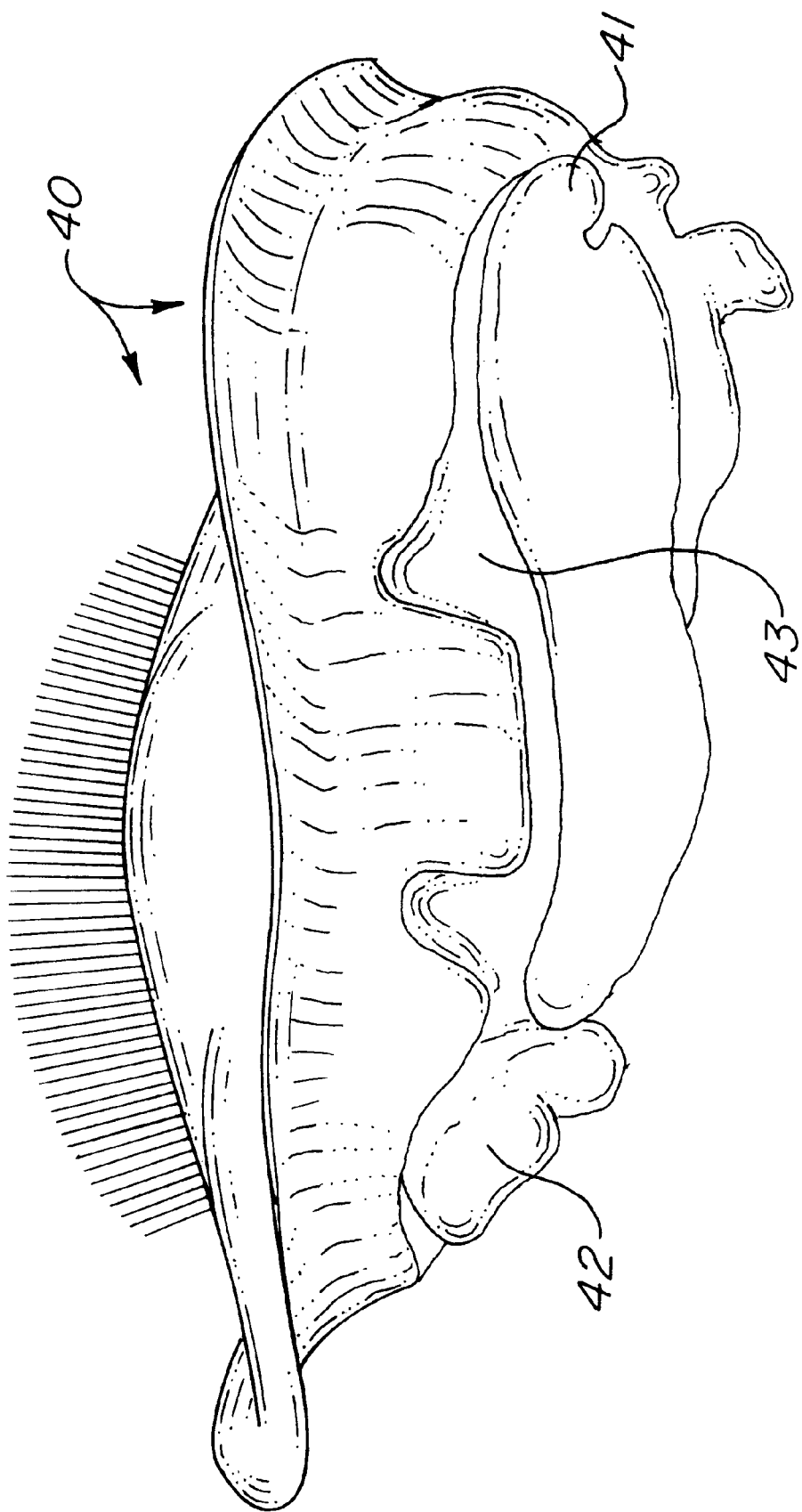
FIG. 10. is a top plan view of the prosthesis formed from the mold of FIG. 6.
Figure 14:
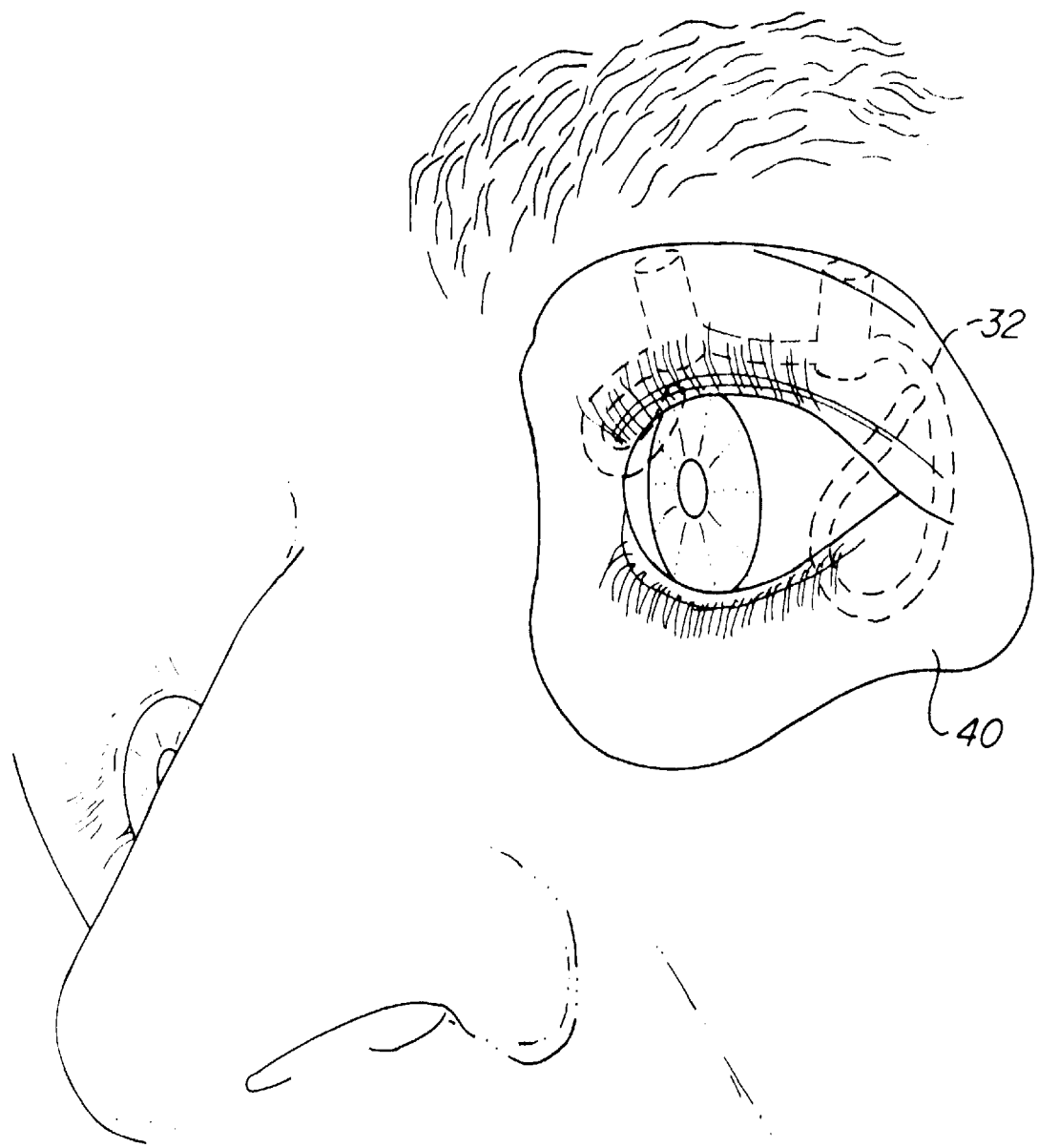
FIG. 14 is a perspective view of a patient with prosthesis in place showing the osseointegrated fixture in hidden lines.

As shown in FIGS. 9 and 10, a prosthesis 40 molded in this fashion has a pair of protuberances 41, 42 which are somewhat mushroom shaped as defined by a groove 43 formed from the cast image of the looped bar 22. The prosthesis, taken in RTV silicone or similar material, is somewhat elastic. The elastic protuberances 41, 42 fit snap-wise into the two loops 24 in the bar 22, thereby holding the prosthesis in position on the patient as shown in FIG. 14.

Although the preferred embodiment is described herein with two loops 24, other applications may desirably employ a greater number of loops 24 and may employ a number of osseointegrated fixtures 32.

It is significant that in the present invention the bar 22 may be attached to the fixtures posteriorly. In the prior art the placement is anteriorly which limits the space available to the prosthesis and thus complicates the task of duplicating the patient's anatomy. For example, in the case of orbital prostheses, the prosthetic eye must be in the same plane as the natural eye for a natural appearance. The approach of the present invention leads to a comfortable fit, good aesthetics, and in the case of orbital prostheses, the ability to maintain a tight fit which allows the maintenance of healthful humidity behind the prosthesis.

Figure 12:
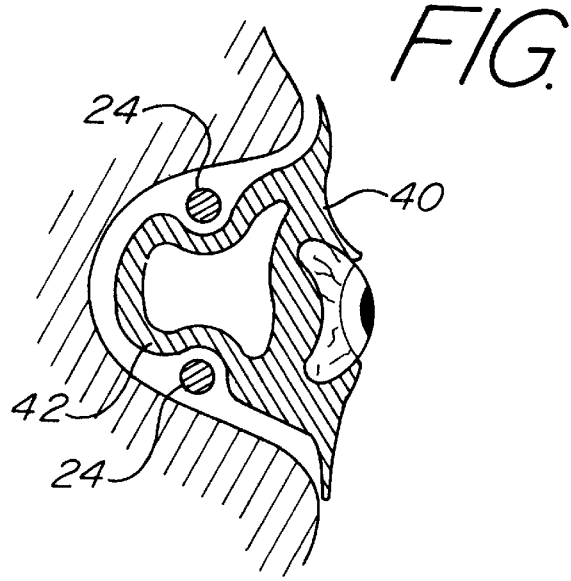
FIG. 12 is an cross section view in elevation along an anterior-posterior plane of the site of FIG. 4 or FIG. 14.
Figure 13:
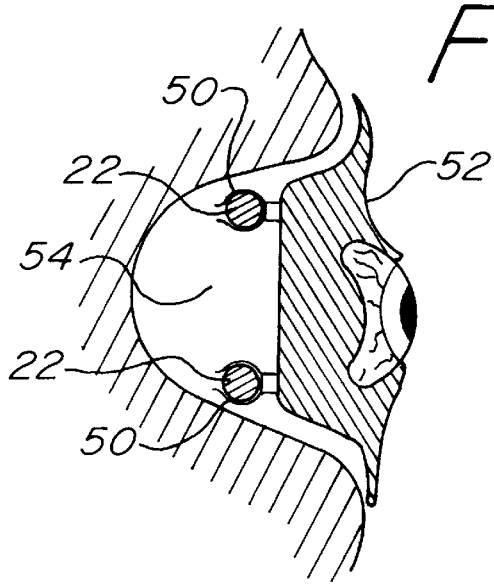
FIG. 13 is a view of the prior art analogous to FIG. 12.

Furthermore, as shown in FIGS. 12 and 13, the prosthesis 52 of the prior art method of attachment employs metallic clips 50 that snap over the bar 22. The prior art prosthesis therefore is located entirely anteriorly to the bar 22 and thus looses the use of the space 54 located posteriorly to the bar 22. In the present invention by contrast, the prosthesis 40 is attached by snapwise fitting of a protuberance (for example protuberance 42) into a loop 24 of the bar 22. As shown in FIG. 12, this allows full use to be made of the space that would normally be unused in the prior art method of attachment. The prosthesis 40 more closely conforms to the patient's anatomy, which may be significant where the prosthesis 40 is not employed for aesthetic purposes, but also provides a replication of function lost with the patient's natural anatomy.

Figure 11:
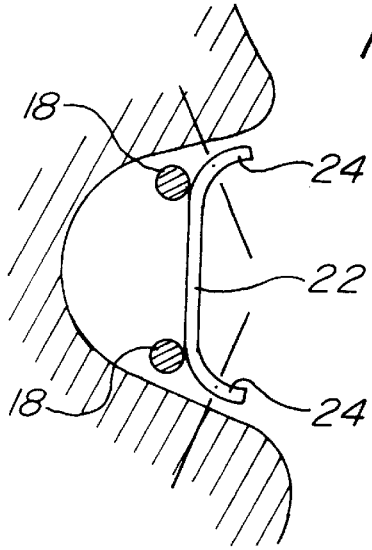
FIG. 11 is a top cross section view of the site of FIG. 4 showing the placement of loops in different planes.

The loops 22 may be formed so as to lie in a single plane. Desirably, however, as shown in FIG. 11, the loops 22 are formed so the loops do not all lie in the same plane. This is advantageous in that the loops 22 provide additional holding leverage. For example, if the prosthesis is an orbital prosthesis, it is desirable that the loops 22 are angled together so that the loops 22 act to hold the prosthesis 40 both in an anterior-posterior direction, but also mediolaterally as well. Not only is the holding power of the fixture 32 increased with respect to the prosthesis 40, but the hold is more evenly distributed so as to place less concentrated stress on the flange fixtures 14.

The present invention has been described with reference to certain preferred and alternative embodiments that are intended to be exemplary only and not limiting to the full scope of the present invention as set forth in the appended claims.

What is claimed is:

1. The combination comprising: a prosthesis and an osseointegrated fixture for the attachment of the prosthesis, wherein said osseointegrated fixture comprises two or more percutaneous osseointegrated implants, a bar affixed to said percutaneous osseointegrated implants, said bar comprising one or more loops; and further wherein said prosthesis comprises one or more elastic mushroom-headed protuberances complementary to said one or more loops for snapwise insertion of said protuberances into said loops.

2. The combination of claim 1, comprising two or more loops and further wherein not all of said two or more loops lie in the same plane.

* * * * *